(12) United States Patent
Kheradvar et al.

(10) Patent No.: US 12,708,758 B2
(45) Date of Patent: Aug. 18, 2026

(54) DISTENSIBLE KNITTED WIRE MESH FOR A CARDIAC SLEEVE

(71) Applicant: THE REGENTS OF THE UNIVERSITY OF CALIFORNIA, Oakland, CA (US)

(72) Inventors: Arash Kheradvar, Irvine, CA (US); Gregory S. Kelley, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 589 days.

(21) Appl. No.: 18/170,341

(22) Filed: Feb. 16, 2023

(65) Prior Publication Data

US 2023/0256232 A1 Aug. 17, 2023

Related U.S. Application Data

(60) Provisional application No. 63/310,717, filed on Feb. 16, 2022.

(51) Int. Cl.

*A61M 60/191* (2021.01)
*A61M 60/289* (2021.01)
*A61M 60/473* (2021.01)
*A61M 60/839* (2021.01)
*A61M 60/863* (2021.01)

(52) U.S. Cl.

CPC ........ *A61M 60/191* (2021.01); *A61M 60/289* (2021.01); *A61M 60/473* (2021.01); *A61M 60/839* (2021.01); *A61M 60/863* (2021.01)

(58) Field of Classification Search

CPC .............. A61M 60/191; A61M 60/863; A61M 60/298; A61M 60/839; A61M 60/473

See application file for complete search history.

(56) References Cited

U.S. PATENT DOCUMENTS 5,702,343 A * 12/1997 Alferness ............ A61M 60/161 600/37
5,800,528 A * 9/1998 Lederman ........... A61M 60/865 623/2.11
5,879,375 A 3/1999 Larson, Jr. et al.
6,309,379 B1 10/2001 Willard et al.

(Continued)

FOREIGN PATENT DOCUMENTS

WO 2013/059747 A1 4/2013
WO 2020/168081 A1 8/2020
WO 2020236750 A1 11/2020

OTHER PUBLICATIONS

USPTO, "Non-Final Office Action", issued in connection with U.S. Appl. No. 17/088,989, dated Apr. 11, 2025, 18 pages.

(Continued)

*Primary Examiner* — Lindsey G Wehrheim

(74) *Attorney, Agent, or Firm* — NGUYEN TARBET IP LAW

(57) ABSTRACT

Heart failure (HF) is a global pandemic affecting at least 26 million people worldwide. Thus, methods and devices that reduce the clinical and economic burden of HF are critical. The present invention features an adjustable cardiac sleeve comprising a basal ring structure and an apical hub couple together, wherein the basal ring structure comprises a plurality of interconnected loops made from a distensible wire.

19 Claims, 6 Drawing Sheets

(56) References Cited

U.S. PATENT DOCUMENTS

Figure 4A:
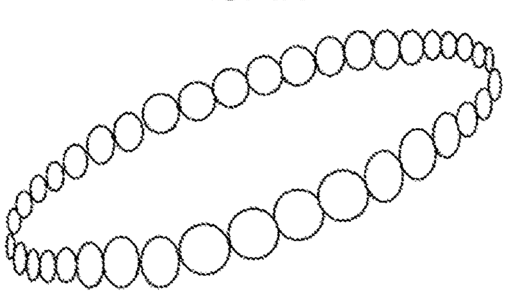

| | | | | |
|---|---|---|---|---|
| 6,984,201 | B2 | 1/2006 | Khaghani et al. | |
| 7,491,170 | B2 | 2/2009 | Gharib | |
| 7,524,298 | B2 | 4/2009 | Gharib et al. | |
| 7,749,152 | B2 | 7/2010 | Gharib et al. | |
| 7,883,325 | B2 | 2/2011 | Kheradvar et al. | |
| 8,075,471 | B2 | 12/2011 | Trumble | |
| 8,133,270 | B2 | 3/2012 | Kheradvar et al. | |
| 8,794,937 | B2 | 8/2014 | Kheradvar et al. | |
| 9,370,425 | B2 * | 6/2016 | Hjelle | A61M 60/839 |
| 9,656,009 | B2 | 5/2017 | Kheradvar et al. | |
| 10,835,713 | B2 | 11/2020 | Homsy et al. | |
| 11,413,144 | B2 | 8/2022 | Rothstein et al. | |
| 2001/0041850 | A1 | 11/2001 | Brenneman et al. | |
| 2001/0047122 | A1 | 11/2001 | Vanden Hoek et al. | |
| 2002/0045799 | A1 | 4/2002 | Lau et al. | |
| 2005/0137682 | A1 | 6/2005 | Justino | |
| 2005/0240200 | A1 | 10/2005 | Bergheim | |
| 2005/0278010 | A1 | 12/2005 | Richardson | |
| 2006/0020377 | A1 | 1/2006 | Goetz et al. | |
| 2006/0043191 | A1 | 3/2006 | Patel et al. | |
| 2006/0167334 | A1 | 7/2006 | Anstadt et al. | |
| 2006/0259137 | A1 | 11/2006 | Artof et al. | |
| 2007/0005131 | A1 | 1/2007 | Taylor | |
| 2007/0015958 | A1 | 1/2007 | Lau et al. | |
| 2007/0021826 | A1 | 1/2007 | Case et al. | |
| 2007/0038291 | A1 | 2/2007 | Case et al. | |
| 2007/0185369 | A1 | 8/2007 | Mirhoseini et al. | |
| 2007/0197859 | A1 | 8/2007 | Schaer et al. | |
| 2007/0203560 | A1 | 8/2007 | Forster et al. | |
| 2007/0208215 | A1 * | 9/2007 | Hjelle | A61F 2/2481 600/37 |
| 2007/0239254 | A1 | 10/2007 | Chia et al. | |
| 2008/0046016 | A1 | 2/2008 | Ben-David et al. | |
| 2008/0228266 | A1 | 9/2008 | McNamara et al. | |
| 2009/0036730 | A1 * | 2/2009 | Criscione | A61M 60/468 600/37 |
| 2009/0131740 | A1 | 5/2009 | Gharib | |
| 2009/0264989 | A1 | 10/2009 | Bonhoeffer et al. | |
| 2009/0281619 | A1 | 11/2009 | Le et al. | |
| 2011/0019886 | A1 | 1/2011 | Mizuno | |
| 2011/0144690 | A1 | 6/2011 | Bishop et al. | |
| 2012/0165916 | A1 | 6/2012 | Jordan | |
| 2012/0283820 | A1 | 11/2012 | Tseng et al. | |
| 2013/0030519 | A1 | 1/2013 | Tran et al. | |
| 2013/0046377 | A1 | 2/2013 | Cohn | |
| 2013/0110895 | A1 | 5/2013 | Valentino et al. | |
| 2013/0243288 | A1 | 9/2013 | Goto | |
| 2013/0310923 | A1 | 11/2013 | Kheradvar et al. | |
| 2014/0107768 | A1 | 4/2014 | Venkatsubramanian | |
| 2014/0228943 | A1 | 8/2014 | Stigall et al. | |
| 2014/0316518 | A1 | 10/2014 | Kheradvar et al. | |
| 2014/0336743 | A1 | 11/2014 | Zotz | |
| 2014/0350350 | A1 | 11/2014 | Imagawa et al. | |
| 2015/0057488 | A1 | 2/2015 | Yomtov | |
| 2016/0045316 | A1 | 2/2016 | Braido et al. | |
| 2016/0206798 | A1 | 7/2016 | Williams et al. | |
| 2017/0080137 | A1 | 3/2017 | Criscione et al. | |
| 2017/0086974 | A1 | 3/2017 | Lashinski et al. | |
| 2017/0296055 | A1 | 10/2017 | Gardner et al. | |
| 2017/0319333 | A1 | 11/2017 | Tegels et al. | |
| 2018/0214266 | A1 | 8/2018 | Paul et al. | |
| 2018/0245243 | A1 | 8/2018 | Krieger et al. | |
| 2018/0300875 | A1 | 10/2018 | Imasugi | |
| 2019/0060542 | A1 | 2/2019 | Atlman et al. | |
| 2019/0133764 | A1 | 5/2019 | Carr et al. | |
| 2019/0282360 | A1 | 9/2019 | Colavito et al. | |
| 2019/0336280 | A1 | 11/2019 | Naor et al. | |
| 2020/0078002 | A1 | 3/2020 | Hacohen et al. | |
| 2020/0226422 | A1 | 7/2020 | Li et al. | |
| 2021/0275299 | A1 | 9/2021 | Peterson et al. | |
| 2021/0330457 | A1 | 10/2021 | Colavito et al. | |
| 2022/0183830 | A1 | 6/2022 | Tseng et al. | |
| 2022/0233307 | A1 | 7/2022 | Tuval et al. | |

OTHER PUBLICATIONS

USPTO, "Non-Final Office Action", issued in connection with U.S. Appl. No. 17/680,636, dated Mar. 4, 2025, 16 pages.

Best, Kate E., and Judith Rankin. "Long-term survival of individuals born with congenital heart disease: a systematic review and meta-analysis." Journal of the American Heart Association 5.6 (2016): e002846.

Hoffman et al. "The incidence of congenital heart disease." Journal of the American college of cardiology 39.12 (2002): 1890-1900.

Dolk et al. "Congenital heart defects in Europe: prevalence and perinatal mortality, 2000 to 2005." Circulation 123.8 (2011): 841-849.

Oster, Matthew E., et al. "Temporal Trends in Survival Among Infants With Critical Congenital Heart Defects." Pediatrics 131.5 (2013): e1502-e1508.

Reller et al. "Prevalence of Congenital Heart Defects in Metropolitan Atlanta, 1998-2005." The Journal of pediatrics 153.6 (2008): 807.

Gilboa et al. "Congenital heart defects in the United States: estimating the magnitude of the affected population in 2010." Circulation 134.2 (2016): 101-109.

Liu et al. "Global birth prevalence of congenital heart defects 1970-2017: updated systematic review and meta-analysis of 260 studies." International journal of epidemiology 48.2 (2019): 455-463.

Davlouros et al. "The right ventricle in congenital heart disease." Heart 92 (2006): i27-i38.

Cho, Young Kuk, and Jae Sook Ma. "Right ventricular failure in congenital heart disease." Korean journal of pediatrics 56.3 (2013): 101.

Voelkel, et al. "Right ventricular function and failure: report of a National Heart, Lung, and Blood Institute working group on cellular and molecular mechanisms of right heart failure." Circulation 114.17 (2006): 1883-1891.

Haddad et al. "Right ventricular function in cardiovascular disease, part I: anatomy, physiology, aging, and functional assessment of the right ventricle." Circulation 117.11 (2008): 1436-1448.

Corno, Antonio F. "Pulmonary valve regurgitation: Neither interventional nor surgery fits all." Frontiers in Pediatrics 6 (2018): 169.

Martin et al. "Safety and feasibility of melody transcatheter pulmonary valve replacement in the native right ventricular butflow tract: a multicenter pediatric heart network scholar study." JACC: Cardiovascular Interventions 11.16 (2018): 1642-1650.

Zheng et al. "Long-term outcome of correction of tetralogy of Fallot in 56 adult patients." Chinese medical journal 126.19 (2013): 3675-3679.

Mitropoulos, et al. "Pulmonary valve replacement in patients with corrected tetralogy of Fallot." Journal of Cardiovascular and Thoracic Research 9.2 (2017): 71.

Warner et al. "Expanding the indications for pulmonary valve replacement after repair of tetralogy of Fallot." The Annals of thoracic surgery 76.4 (2003): 1066-1071.

Stern, Menachem, Matthew B. Pinson, and Arvind Murugan. "The complexity of folding self-folding origami." Physical Review X 7.4 (2017): 041070.

Peraza Hernandez, E. A., D. J. Hartl, and D. C. Lagoudas. "Design and simulation of origami structures with smooth folds." Proceedings of the Royal Society A: Mathematical, Physical and Engineering Sciences 473.2200 (2017): Jul. 16, 2016.

Schlickenrieder, Wolfram. "Nets of polyhedra." Master's Thesis, Technische Universität Berlin (1997).

Krankenberg et al. "Self-expanding versus balloon-expandable stents for iliac artery occlusive disease: the randomized ICE trial." JACC: Cardiovascular Interventions 10.16 (2017): 1694-1704.

Kheradvar et al. "Proof of concept of Foldavalve, a novel 14 Fr totally repositionable and retrievable transcatheter aortic valve." EuroIntervention: journal of EuroPCR in collaboration with the Working Group on Interventional Cardiology of the European Society of Cardiology 11.5 (2015): 591-596.

Yi et al. "Bioinspired reversible hydrogel adhesives for wet and underwater surfaces." Journal of Materials Chemistry B 6.48 (2018): 8064-8070.

(56) References Cited

OTHER PUBLICATIONS

Zhao et al. "Bio-inspired reversible underwater adhesive." Nature communications 8.1 (2017): 1-8.
Lee, Haeshin, Bruce P. Lee, and Phillip B. Messersmith. "A reversible wet/dry adhesive inspired by mussels and geckos." Nature 448.7151 (2007): 338-341.
Cho et al. "Intrinsically reversible superglues via shape adaptation inspired by snail epiphragm." Proceedings of the National Academy of Sciences 116.28 (2019): 13774-13779.
Cools et al. "Medium term follow-up after percutaneous pulmonary valve replacement with the Melody® valve." IJC Heart & Vasculature 7 (2015): 92-97.
Zareian et al. "Effect of stent crimping on calcification of transcatheter aortic valves." Interactive cardiovascular and thoracic surgery 29.1 (2019): 64-73.
Lepidi et al. "Quantitative histological examination of bioprosthetic heart valves." Clinical infectious diseases 42.5 (2006): 590-596.
Lepidi et al. "Quantitative analysis of valvular lesions during Bartonella endocarditis." American journal of clinical pathology 114.6 (2000): 880-889.
Sellers et al. "Transcatheter aortic heart valves: histological analysis providing insight to leaflet thickening and structural valve degeneration." JACC: Cardiovascular Imaging 12.1 (2019): 135-145.
Martin, Caitlin, and Wei Sun. "Biomechanical characterization of aortic valve tissue in humans and common animal models." Journal of biomedical materials research. Part A 100.6 (2012).
Jiao et al. "Measurements of the Effects of Decellularization on Viscoelastic Properties of Tissues in Ovine, Baboon, and Human Heart Valves." Tissue Engineering. Part A 18.3-4 (2012): 423.
White et al. "Heart valve collagens: cross-species comparison using immunohistological methods." Journal of Heart Valve Disease 19.6 (2010): 766.
McCoy et al. "Sex-related differences in gene expression by porcine aortic valvular interstitial cells." PloS one 7.7 (2012): e39980.
Choo et al. "Development of an animal experimental model for a bileaflet mechanical heart valve prosthesis." Journal of Korean medical science 19.1 (2004): 37-41.
Capulli et al. "JetValve: Rapid manufacturing of biohybrid scaffolds for biomimetic heart valve replacement." Biomaterials 133 (2017): 229-241.
Ropcke et al. "Small intestinal submucosa tricuspid valve tube graft shows growth potential, remodelling and physiological valve function in a porcine model." Interactive CardioVascular and Thoracic Surgery 24.6 (2017): 918-924.
Yoon et al. "Outcomes of transcatheter mitral valve replacement for degenerated bioprostheses, failed annuloplasty rings, and mitral annular calcification." European heart journal 40.5 (2019): 441-451.
Guerrero et al. "1-year outcomes of transcatheter mitral valve replacement in patients with severe mitral annular calcification." Journal of the American College of Cardiology 71.17 (2018): 1841-1853.
Khan, Jaffar M., et al. "Anterior leaflet laceration to prevent ventricular outflow tract obstruction during transcatheter mitral valve replacement." Journal of the American College of Cardiology 73.20 (2019): 2521-2534.
Blanke et al. "Predicting LVOT obstruction in transcatheter mitral valve implantation: concept of the neo-LVOT." JACC: Cardiovascular Imaging 10.4 (2017): 482-485.
Khan et al. ""Rescue" Lampoon to Treat Transcatheter Mitral Valve Replacement-Associated Left Ventricular Outflow Tract Obstruction." JACC: Cardiovascular Interventions 12.13 (2019): 1283-1284.
Khan et al. "Lampoon to facilitate Tendyne transcatheter mitral valve replacement." JACC: Cardiovascular Interventions 11.19 (2018): 2014-2017.
Greenbaum et al. "Long or redundant leaflet complicating transcatheter mitral valve replacement: case vignettes that advocate for removal or reduction of the anterior mitral leaflet." Catheterization and Cardiovascular Interventions 92.3 (2018): 627-632.
Leon MB, et al. "Transcatheter aortic-valve implantation for aortic stenosis in patients who cannot undergo surgery" 2010 The New England Journal of Medicine 363:1597-1607.
Mack, Michael J. "Does transcatheter aortic valve implantation mean the end of surgical aortic valve replacement?." Texas Heart Institute Journal 37.6 (2010): 658.
Cribier et al. "Percutaneous transcatheter implantation of an aortic valve prosthesis for calcific aortic stenosis: first human case description." Circulation 106.24 (2002): 3006-3008.
Makkar, et al. "Transcatheter aortic-valve replacement for inoperable severe aortic stenosis." New England Journal of Medicine 366.18 (2012): 1696-1704.
Geisbüsch et al. "Incidence and management of CoreValve dislocation during transcatheter aortic valve implantation." Circulation: Cardiovascular Interventions 3.6 (2010): 531-536.
Thomas et al. "Thirty-day results of the Sapien aortic Bioprosthesis European Outcome (Source) Registry: a European registry of transcatheter aortic valve implantation using the Edwards Sapien valve." Circulation 122.1 (2010): 62-69.
Ussia, et al. "The valve-in-valve technique for treatment of aortic bioprosthesis malposition: an analysis of incidence and 1-year clinical outcomes from the Italian CoreValve registry." Journal of the American College of Cardiology 57.9 (2011): 1062-1068.
Masson et al. "Transcatheter aortic valve implantation: review of the nature, management, and avoidance of procedural complications." JACC: Cardiovascular Interventions 2.9 (2009): 811-820.
Webb, John G., et al. "Transcatheter valve-in-valve implantation for failed bioprosthetic heart valves." Circulation 121.16 (2010): 1848-1857.
Gurvitch et al. "Transcatheter valve-in-valve implantation for failed surgical bioprosthetic valves." Journal of the American College of Cardiology 58.21 (2011): 2196-2209.
Groves et al. "The effects of positioning of transcatheter aortic valve on fluid dynamics of the aortic root." ASAIO Journal (American Society for Artificial Internal Organs: 1992) 60.5 (2014): 545.
Su, Jimmy Li-Shin, Bo Wang, and Stanislav Y. Emelianov. "Photoacoustic imaging of coronary artery stents." Optics Express 17.22 (2009): 19894-19901.
Elgort, et al. "Image-guided and-monitored renal artery stenting using only MRI." Journal of Magnetic Resonance Imaging: An Official Journal of the International Society for Magnetic Resonance in Medicine 23.5 (2006): 619-627.
De Heer et al. "Multimodality imaging throughout transcatheter aortic valve implantation." Future Cardiology 8.3 (2012): 413-424.
Jilaihawi et al. "Cross-sectional computed tomographic assessment improves accuracy of aortic annular sizing for transcatheter aortic valve replacement and reduces the incidence of paravalvular aortic regurgitation." Journal of the American College of Cardiology 59.14 (2012): 1275-1286.
Willson et al. "3-dimensional aortic annular assessment by multidetector computed tomography predicts moderate or severe paravalvular regurgitation after transcatheter aortic valve replacement: a multicenter retrospective analysis." Journal of the American College of Cardiology 59.14 (2012): 1287-1294.
Jilaihawi et al. "A revised methodology for aortic-valvar complex calcium quantification for transcatheter aortic valve implantation." Eur Heart J Cardiovasc Imaging. Dec. 2014;15(12):1324-32.
White et al. "The role of cinefluoroscopy and intravascular ultrasonography in evaluating the deployment of experimental endovascular prostheses." Journal of vascular surgery 21.3 (1995): 365-374.
Moss et al. "Role of echocardiography in percutaneous aortic valve implantation." JACC: Cardiovascular Imaging 1.1 (2008): 15-24.
Naqvi, Tasneem Z. "Echocardiography in percutaneous valve therapy." JACC: Cardiovascular Imaging 2.10 (2009): 1226-1237.
Dumont et al. "Feasibility of transapical aortic valve implantation fully guided by transesophageal echocardiography." The Journal of Thoracic and Cardiovascular Surgery 138.4 (2009): 1022-1024.
Jánosi et al. "Guidance of percutaneous transcatheter aortic valve implantation by real-time three-dimensional transesophageal echocardiography—A single-center experience." Minimally Invasive Therapy & Allied Technologies 18.3 (2009): 142-148.

(56) References Cited

OTHER PUBLICATIONS

Bartel et al. "Intracardiac echocardiography for guidance of transcatheter aortic valve implantation under monitored sedation: a solution to a dilemma?." European Heart Journal-Cardiovascular Imaging 17.1 (2016): 1-8.
Sengupta et al. "Transthoracic echocardiography guidance for TAVR under monitored anesthesia care." Cardiovascular Imaging 8.3 (2015): 379-380.
Choi et al. "Relationship between coronary artery calcium score by multidetector computed tomography and plaque components by virtual histology intravascular ultrasound." Journal of Korean medical science 26.8 (2011): 1052-1060.
Kpodonu, Jacques, Venkatesh G. Ramaiah, and Edward B. Diethrich. "Intravascular ultrasound imaging as applied to the aorta: a new tool for the cardiovascular surgeon." The Annals of thoracic surgery 86.4 (2008): 1391-1398.
Mintz et al. "American College of Cardiology clinical expert consensus document on standards for acquisition, measurement and reporting of intravascular ultrasound studies (ivus) A report of the american college of cardiology task force on clinical expert consensus documents developed in collaboration with the european society of cardiology endorsed by the society of cardiac angiography and interventions." Journal of the American College of Cardiology 37.5 (2001): 1478-1492.
Ferrari et al. "Imaging for trans-catheter pulmonary stent-valve implantation without angiography: role of intravascular ultrasound." European journal of cardio-thoracic surgery 40.2 (2011): 522-524.
Mathur, S. K., and Pooja Singh. "Transoesophageal echocardiography related complications." Indian Journal of Anaesthesia 53.5 (2009): 567.
Jánosi et al. "Quantitative analysis of aortic valve stenosis and aortic root dimensions by three-dimensional echocardiography in patients scheduled for transcutaneous aortic valve implantation." Current cardiovascular imaging reports 7.11 (2014): 1-9.
Maragiannis, Dimitrios, and Stephen H. Little. "Interventional imaging: the role of echocardiography." Methodist DeBakey cardiovascular journal 10.3 (2014): 172.
Klein, Andrew A., Nikolas J. Skubas, and Joerg Ender. "Controversies and complications in the perioperative management of transcatheter aortic valve replacement." Anesthesia & Analgesia 119.4 (2014): 784-798.
Klein et al. "Economic analysis of a transesophageal echocardiography-guided approach to cardioversion of patients with atrial fibrillation: the Acute economic data at eight weeks." Journal of the American College of Cardiology 43.7 (2004): 1217-1224.
Roy et al. "First-in-man use of aortic valve ultrasound for assessment of aortic valve anatomy pre-and post-transcatheter aortic valve implantation." JACC: Cardiovascular Interventions 6.6 (2013): 634-635.
Kheradvar et al. "Emerging trends in heart valve engineering: Part IV. Computational modeling and experimental studies." Annals of biomedical engineering 43.10 (2015): 2314-2333.
Kahlert et al. "Towards real-time cardiovascular magnetic resonance guided transarterial CoreValve implantation: in vivo evaluation in swine." Journal of Cardiovascular Magnetic Resonance 14.1 (2012): 1-15.
Kapadia et al. "Imaging for transcatheter valve procedures." Current problems in cardiology 35.5 (2010): 228-276.
Kheradvar, Arash, and Morteza Gharib. "On mitral valve dynamics and its connection to early diastolic flow." Annals of biomedical engineering 37.1 (2009): 1-13.
Kheradvar et al. "An in vitro study of changing profile heights in mitral bioprostheses and their influence on flow." Asaio Journal 52.1 (2006): 34-38.
Kheradvar, Arash, Michele Milano, and Morteza Gharib. "Correlation between vortex ring formation and mitral annulus dynamics during ventricular rapid filling." Asaio Journal 53.1 (2007): 8-16.
Tsukui et al. "Cerebrovascular accidents in patients with a ventricular assist device." The Journal of thoracic and cardiovascular surgery 134.1 (2007): 114-123.
Kirklin et al. "Fifth Intermacs annual report: risk factor analysis from more than 6,000 mechanical circulatory support patients." The Journal of heart and lung transplantation 32.2 (2013): 141-156.
Starling et al. "Unexpected abrupt increase in left ventricular assist device thrombosis." New England Journal of Medicine 370.1 (2014): 33-40.
Kirklin et al. "Interagency Registry for Mechanically Assisted Circulatory Support (Intermacs) analysis of pump thrombosis in the HeartMate II left ventricular assist device." The Journal of Heart and Lung Transplantation 33.1 (2014): 12-22.
Rigatelli, Gianluca, Francesco Santini, and Giuseppe Faggian. "Past and present of cardiocirculatory assist devices: a comprehensive critical review." Journal of Geriatric Cardiology: JGC 9.4 (2012): 389.
Almond, Christopher S. "The FDA review process for cardiac medical devices in children: a review for the clinician." Progress in pediatric cardiology 33.2 (2012): 105-109.
Grosberg, Anna, Morteza Gharib, and Arash Kheradvar. "Effect of fiber geometry on pulsatile pumping and energy expenditure." Bulletin of mathematical biology 71.7 (2009): 1580-1598.
Leon et al. "Transcatheter or surgical aortic-valve replacement in intermediate-risk patients." New England Journal of Medicine 374.17 (2016): 1609-1620.
Dvir et al. "Standardized definition of structural valve degeneration for surgical and transcatheter bioprosthetic aortic valves." Circulation 137.4 (2018): 388-399.
Kheradvar, Arash, et al. "Emerging trends in heart valve engineering: Part II. Novel and standard technologies for aortic valve replacement." Annals of biomedical engineering 43.4 (2015): 844-857.
Zegdi et al. "Evidence of leaflet injury during percutaneous aortic valve deployment." European journal of cardio-thoracic surgery 40.1 (2011): 257-260.
De Buhr et al. "Impairment of pericardial leaflet structure from balloon-expanded valved stents." The Journal of Thoracic and Cardiovascular Surgery 143.6 (2012): 1417-1421.
Ong, Sea Hing, Ralf Mueller, and Stein Iversen. "Early calcific degeneration of a CoreValve transcatheter aortic bioprosthesis." European heart journal 33.5 (2012): 586-586.
Harbaoui et al. "Early Edwards Sapien valve degeneration after transcatheter aortic valve replacement." JACC: Cardiovascular Interventions 9.2 (2016): 198-199.
Webb, John G., and Danny Dvir. "Is transcatheter aortic valve replacement a durable therapeutic strategy?." JACC: Cardiovascular Interventions 8.8 (2015): 1092-1094.
Sinha, Aditi, Oleksandr Barannyk, and Arash Kheradvar. "Crimp induced leaflet damage and calcification of transcatheter heart valves." Cardiology 134.2 (2016): 170-171.
Makkar, Raj R., and Tarun Chakravarty. "Transcatheter aortic valve thrombosis: new problem, new insights." JACC: Cardiovascular Interventions 10.7 (2017): 698-700.
Bush, Charles H., John D. Reith, and Suzanne S. Spanier. "Mineralization in Musculoskeletal Leiomyosarcoma: Radiologic-Pathologic Correlation." American Journal of Roentgenology 180.1 (2003): 109-113.
Otto, C. M. "Calcification of bicuspid aortic valves." Heart 88.4 (2002): 321-322.
Alavi, S. Hamed, Elliott M. Groves, and Arash Kheradvar. "The effects of transcatheter valve crimping on pericardial leaflets." The Annals of thoracic surgery 97.4 (2014): 1260-1266.
Dasi, Lakshmi P., et al. "On the mechanics of transcatheter aortic valve replacement." Annals of biomedical engineering 45.2 (2017): 310-331.
Delogne, Christophe, et al. "Characterization of the calcification of cardiac valve bioprostheses by environmental scanning electron microscopy and vibrational spectroscopy." Journal of microscopy 228.1 (2007): 62-77.
Schoen, Frederick J., Jack W. Tsao, and Robert J. Levy. "Calcification of bovine pericardium used in cardiac valve bioprostheses.

(56) References Cited

OTHER PUBLICATIONS

Implications for the mechanisms of bioprosthetic tissue mineralization." The American journal of pathology 123.1 (1986): 134.
Bertazzo et al. "Nano-analytical electron microscopy reveals fundamental insights into human cardiovascular tissue calcification." Nature materials 12.6 (2013): 576-583.
Schoen, Frederick J., and Robert J. Levy. "Calcification of tissue heart valve substitutes: progress toward understanding and prevention." The Annals of thoracic surgery 79.3 (2005): 1072-1080.
Khoffi et al. "Transcatheter fiber heart valve: effect of crimping on material performances." Journal of Biomedical Materials Research Part B: Applied Biomaterials 103.7 (2015): 1488-1497.
Arora et al. "Early transcatheter valve prosthesis degeneration and future ramifications." Cardiovascular Diagnosis and Therapy 7.1 (2017): 1.
Chhatriwalla et al. "Bioprosthetic valve fracture improves the hemodynamic results of valve-in-valve transcatheter aortic valve replacement." Circulation: Cardiovascular Interventions 10.7 (2017): e005216.
Sathananthan et al. "Valve-in-valve transcatheter aortic valve replacement and bioprosthetic valve fracture comparing different transcatheter heart valve designs: an ex vivo bench study." JACC: Cardiovascular Interventions 12.1 (2019): 65-75.
Yuan S-M, Mishaly D, Shinfeld A, Raanani E. Right ventricular outflow tract reconstruction: Valved conduit of choice and clinical outcomes. Journal of Cardiovascular Medicine. 2008;9:327-337.
Gatzoulis MA, Balaji S, Webber SA, Siu SC, Hokanson JS, Poile C, Rosenthal M, Nakazawa M, Moller JH, Gillette PC, Webb GD, Redington AN. Risk factors for arrhythmia and sudden cardiac death late after repair of tetralogy of fallot: A multicentre study. The Lancet. 2000;356:975-981.
Texakalidis P, Giannopoulos S, Kokkinidis DG, Lanzino G. Effect of open—vs closed-cell stent design on periprocedural outcomes and restenosis after carotid artery stenting: A systematic review and comprehensive meta-analysis. Journal of Endovascular Therapy. 2018;25:523-533.
Jalal Z, Galmiche L, Lebeaux D, Villemain O, Brugada G, Patel M, Ghigo J-M, Beloin C, Boudjemline Y. Selective propensity of bovine jugular vein material to bacterial adhesions: An in-vitro study. International Journal of Cardiology. 2015;198:201-205.
Richardt, Doreen, Thorsten Hanke, and Hans-Hinrich Sievers. "Two cases of heart failure after implantation of a CoreValve prosthesis." The New England journal of medicine 372.11 (2015): 1079-1080.
Thielmann, M., et al. "Current developments in transcatheter aortic valve implantation techniques." Herz 36.8 (2011): 696-705.
Svensson, Lars G., et al. "United States feasibility study of transcatheter insertion of a stented aortic valve by the left ventricular apex." The Annals of thoracic surgery 86.1 (2008): 46-55.
Pislaru SV, et al. 2014 Progress in Cardiovascular Diseases 57:32-46.
Bartel T, et al. 2011 Journal of the American Society of Echocardiography 24:966-975.
Okabe, Teruo, et al. "The predictive value of computed tomography calcium scores: a comparison with quantitative volumetric intravascular ultrasound." Cardiovascular Revascularization Medicine 10.1 (2009): 30-35.
Beebe, Hugh G. "Imaging modalities for aortic endografting." Journal of Endovascular Therapy 4.2 (1997): 111-123.
Kawase, Yoshiaki, et al. "In vivo volumetric analysis of coronary stent using optical coherence tomography with a novel balloon occlusion-flushing catheter: a comparison with intravascular ultrasound." Ultrasound in medicine & biology 31.10 (2005): 1343-1349.
Ávila, P., et al. "IVUS guidance in percutaneous closure of aortic paraprosthetic leak." Cardiovascular intervention and therapeutics 27.2 (2012): 137-139.
Alboliras, Ernerio T., and Ziyad M. Hijazi. "Comparison of costs of intracardiac echocardiography and transesophageal echocardiography in monitoring percutaneous device closure of atrial septal defect in children and adults." The American journal of cardiology 94.5 (2004): 690-692.
Falahatpisheh, Ahmad, and Arash Kheradvar. "High-speed particle image velocimetry to assess cardiac fluid dynamics In vitro: From performance to validation." European Journal of Mechanics-B/Fluids 35 (2012): 2-8.
Kiefer, Philipp, et al. "Crimping may affect the durability of transcatheter valves: an experimental analysis." The Annals of thoracic surgery 92.1 (2011): 155-160.
Van Steenberghe, Mathieu, et al. "Early transcatheter aortic valve degeneration in the young." International Journal of Cardiology 222 (2016): 786-787.
Pascual, Isaac, Pablo Avanzas, and César Morís. "Degenerative pattern of a percutaneous aortic valve." Revista espanola de cardiologia (English ed.) 70.9 (2017): 772.
Kapolos et al. "Model experimental system for investigation of heart valve calcification in vitro." Journal of biomedical materials research 38.3 (1997): 183-190.
Krings et al. "Development of a new combined test setup for accelerated dynamic pH-controlled in vitro calcification of porcine heart valves." The International Journal of Artificial Organs 32.11 (2009): 794-801.
Tertti, Risto, et al. "Comparison of calcium phosphate product values using measurement of plasma total calcium and serum ionized calcium." Hemodialysis International 11.4 (2007): 411-416.
Cheng, Ching-Li, et al. "Ex vivo assessment of valve thickness/calcification of patients with calcific aortic stenosis in relation to in vivo clinical outcomes." Journal of the Mechanical Behavior of Biomedical Materials 74 (2017): 324-332.
Foroutan, Farid, et al. "Structural valve deterioration after transcatheter aortic valve implantation." Heart 103.23 (2017): 1899-1905.
Cantwell et al. "Techniques for automated local activation time annotation and conduction velocity estimation in cardiac mapping." Computers in biology and medicine 65 (2015): 229-242.
"Conventional Intracardiac Mapping Techniques"; https://thoracickey.com/conventional-intracardiac-mapping-techniques/; retrieved from web Jul. 1, 2024.
Clayton, Richard H., and Alexander V. Panfilov. "A guide to modelling cardiac electrical activity in anatomically detailed ventricles." Progress in biophysics and molecular biology 96.1-3 (2008): 19-43.
O'Shea et al. "ElectroMap: high-throughput open-source software for analysis and mapping of cardiac electrophysiology." Scientific reports 9.1 (2019): 1389.
USPTO, "Non-Final Office Action", issued in connection with U.S. Appl. No. 17/830,012, dated Jun. 4, 2025, 11 pages.

* cited by examiner

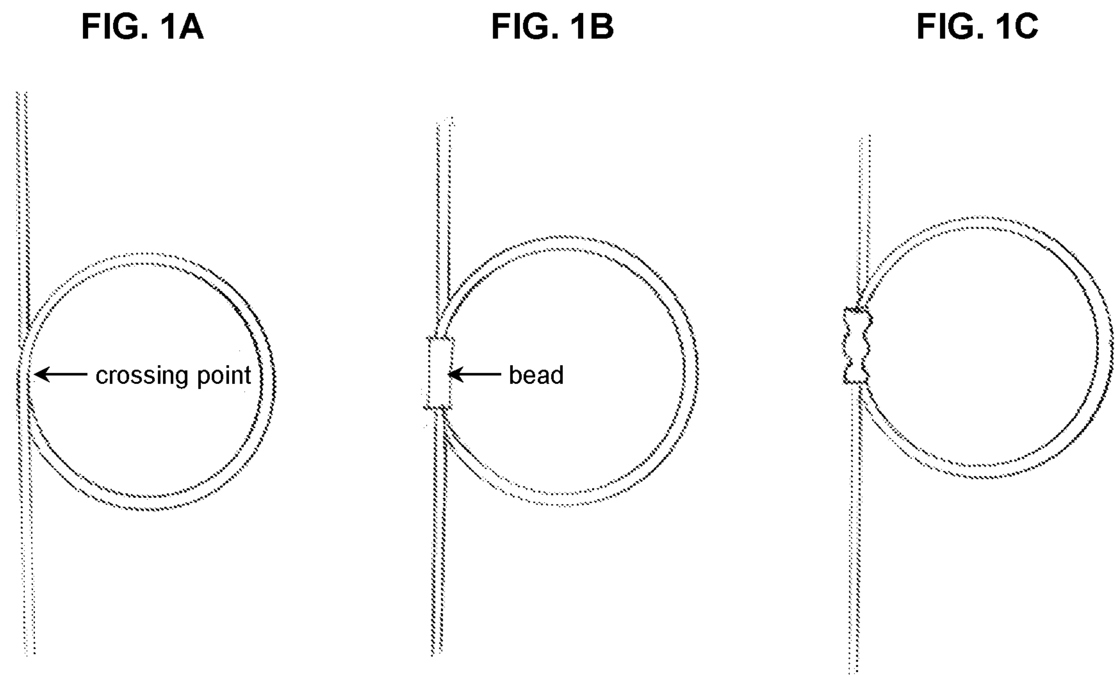
FIG. 1A
crossing point
FIG. 1B
bead
FIG. 1C
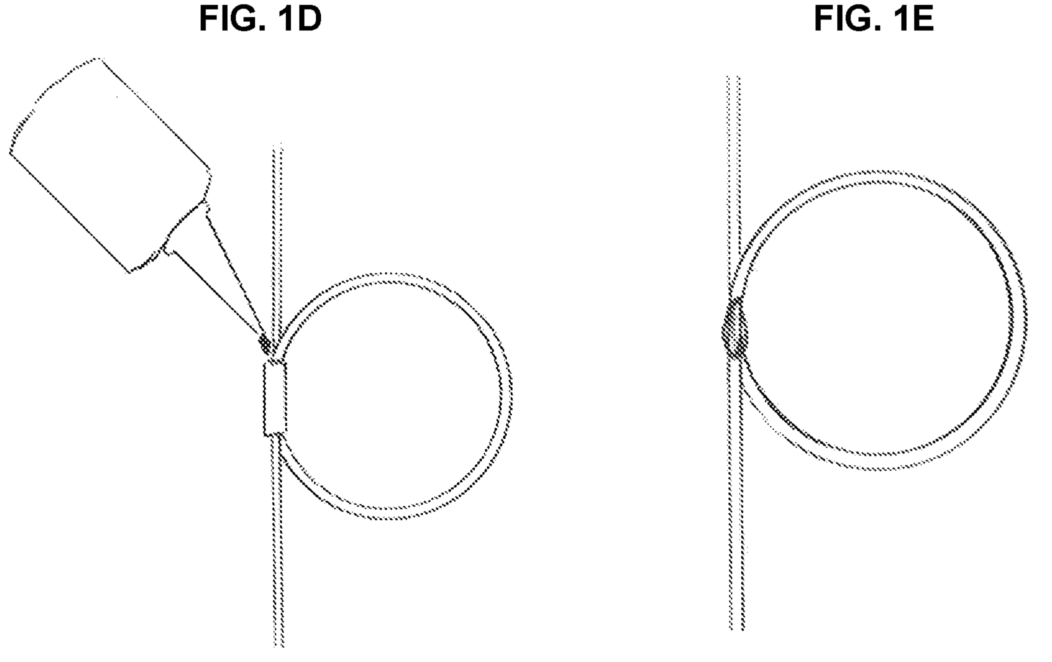
FIG. 1D
FIG. 1E

FIG. 2A
FIG. 2B
FIG. 2C
FIG. 2D
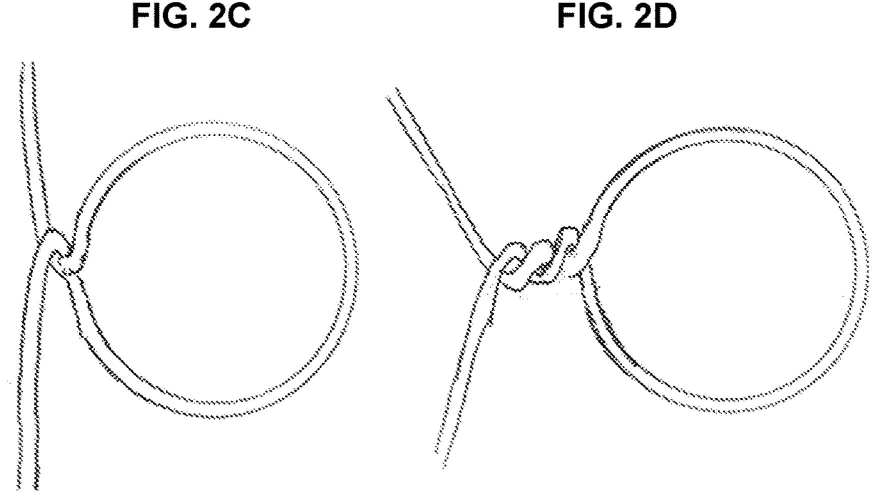
FIG. 3A
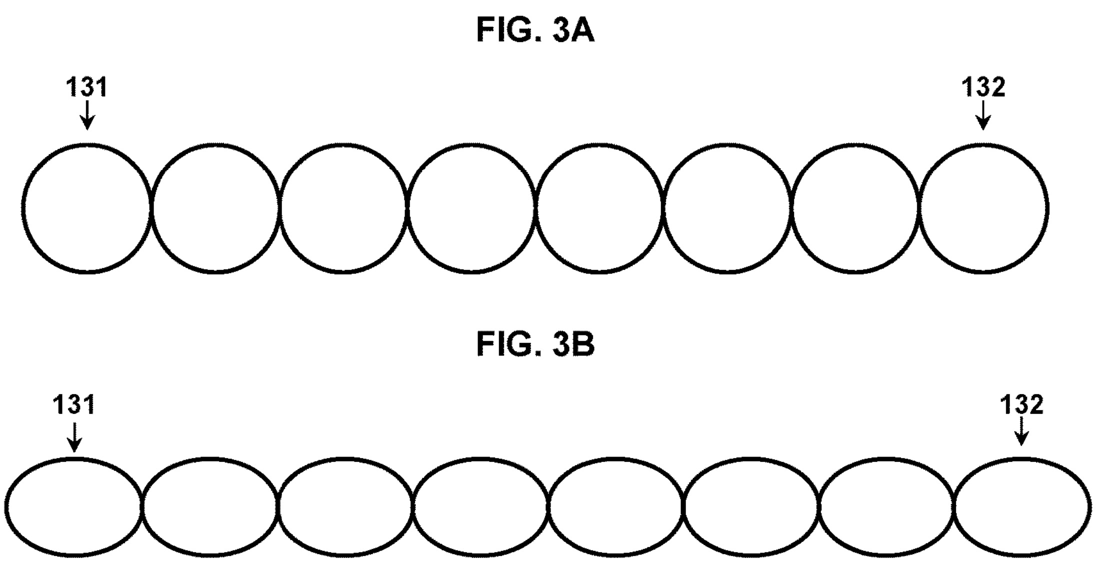
FIG. 3B

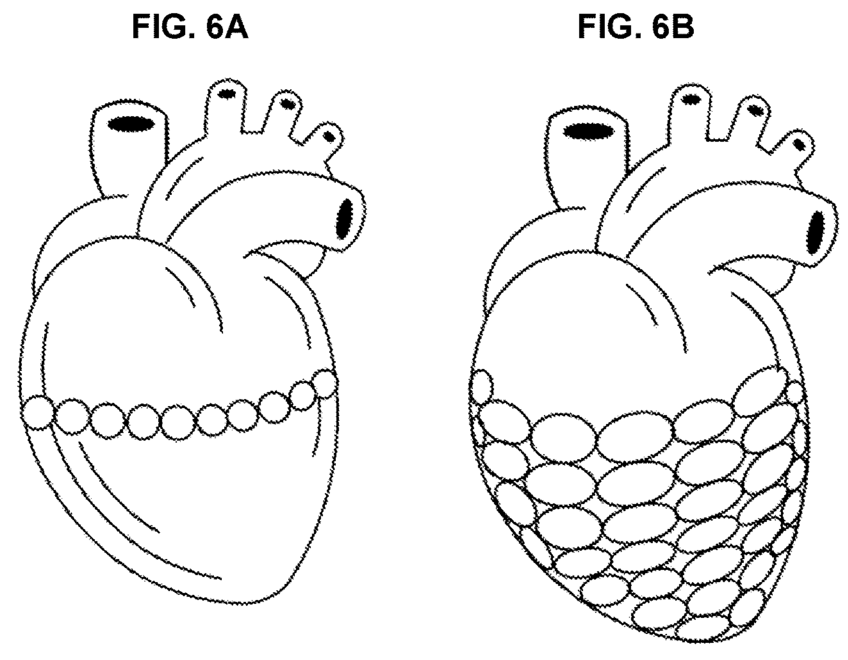
FIG. 6A FIG. 6B
FIG. 7A FIG. 7B FIG. 7C
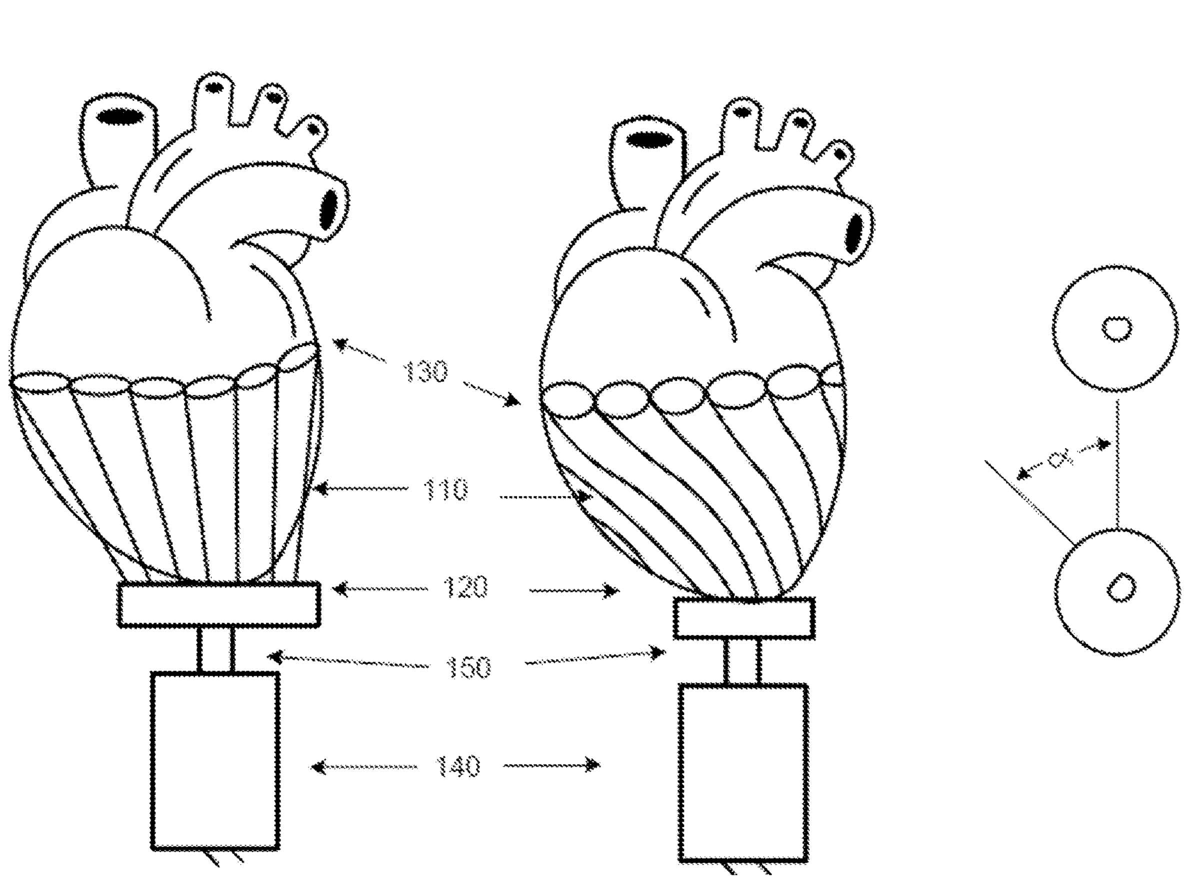

100
150
120
130
100
120
110
130
100
130

DISTENSIBLE KNITTED WIRE MESH FOR A CARDIAC SLEEVE

CROSS-REFERENCES TO RELATED APPLICATIONS

This application is a non-provisional and claims benefit of U.S. Provisional Application No. 63/310,717 filed Feb. 16, 2022, the specification of which is incorporated herein in their entirety by reference.

FIELD OF THE INVENTION

The present invention features devices made of distensible knitted wire mesh for use in a cardiac sleeve device.

BACKGROUND OF THE INVENTION

Regardless of the underlying cause, heart failure (HF) is a global pandemic and generates an enormous clinical and economic burden. As of 2017, HF has a worldwide prevalence estimated at 64.34 million cases. Thus, the economic burden of HF on healthcare systems is considerable and will increase as the prevalence grows. The worldwide economic cost of HF in 2012 was estimated at $108 billion per year, with $65 billion attributed to direct costs and $43 billion to indirect costs. According to the American Heart Association (AHA), in the USA, the total cost of care (direct and indirect costs) for HF in 2020 is estimated at $43.6 billion, and without improvements in outcomes, the annual total cost of care in the USA is projected to increase to $69.7 billion by 2030.

Furthermore, heart failure costs within the seven key markets of the U.S., France, Germany, Italy, Spain, the U.K., and Japan is set to grow from $3.7 billion in 2016 to around $16.1 billion by 2026, per the Global Data research and consulting firm. This represents an impressive compound annual growth rate (CAGR) of 15.7 percent. Thus, finding technologies to reduce HF's clinical and economic burden is critical.

BRIEF SUMMARY OF THE INVENTION

It is an objective of the present invention to provide devices that allow for an adjustable cardiac sleeve that can reversibly collapse into a smaller shape to be further expanded for various uses, such as during the delivery process from one chamber into another chamber, as specified in the independent claims. Embodiments of the invention are given in the dependent claims. Embodiments of the present invention can be freely combined with each other if they are not mutually exclusive.

In some embodiments, the present invention features an adjustable cardiac sleeve comprising a basal ring structure coupled to an apical hub. The basal ring structure may comprise a plurality of interconnected loops made from a distensible wire. The plurality of interconnected loops comprises a first loop end connected to a second loop end to form a ring. In some embodiments, the basal ring structure and the apical hub are interconnected to each other.

In some embodiments, the present invention may feature a method of treating heart failure in a subject in need thereof. The method may comprise obtaining a cardiac sleeve as described herein and externally wrapping over the epicardium of a native, intact heart of the subject. The cardiac sleeve may cycle between a diastolic position and a systolic position.

One of the unique and inventive technical features of the present invention is the use of a plurality of interconnected loops that form a ring to construct the basal ring structure described herein. Without wishing to limit the invention to any theory or mechanism, it is believed that the technical feature of the present invention advantageously provides for cardiac sleeves that can be used where a structure needs to be reversibly collapsed into a smaller shape or to be further expanded for a variety of uses. For example, the diameter of the plurality of interconnected loops may be increased to accommodate a larger heart, e.g., the loops may be elongated (such that the loops form an elliptical shape), or larger circular-shaped loops may be used. None of the presently known prior references or work has the unique, inventive technical feature of the present invention.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIGS. 1A, 1B, 1C, 1D, and 1E demonstrate how a wire is formed into a loop with a crossing point. In certain embodiments, the crossing point of said wire (FIG. 1A) is secured with a bead (FIG. 1B). The bead may further be secured by crimping said bead (FIG. 1C) or by applying an adhesive inside the bead (FIG. 1D). The crossing point of said wire may further be secured by welding (FIG. 1E).

FIGS. 2A, 2B, 2C, and 2D show, in accordance with embodiments herein, how a wire formed into a loop may be secured. The wire loops may be secured with an axial twist (FIG. 2A) or with a plurality of axial twists (FIG. 2B). The wire loop may additionally be secured with an orthogonal twist (FIG. 2C) or a plurality of orthogonal twists (FIG. 2D).

FIGS. 3A and 3B show a structure comprising multiple loops secured together. FIG. 3A shows the multiple loops secured together without tension. FIG. 3B shows how the loops secured together elongate under tension.

Figure 4B:
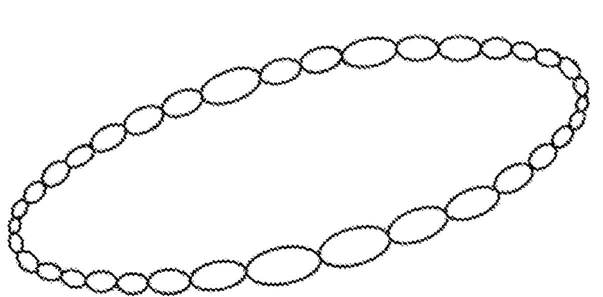

FIGS. 4A and 4B show a closed ring-like structure comprising a plurality of loops secured together, wherein a first loop end is connected to a second loop end. FIG. 4A shows a closed ring-link structure without tension. FIG. 4B shows a closed ring-like structure (e.g., a distensible ring) elongated under tension.

Figure 5A:
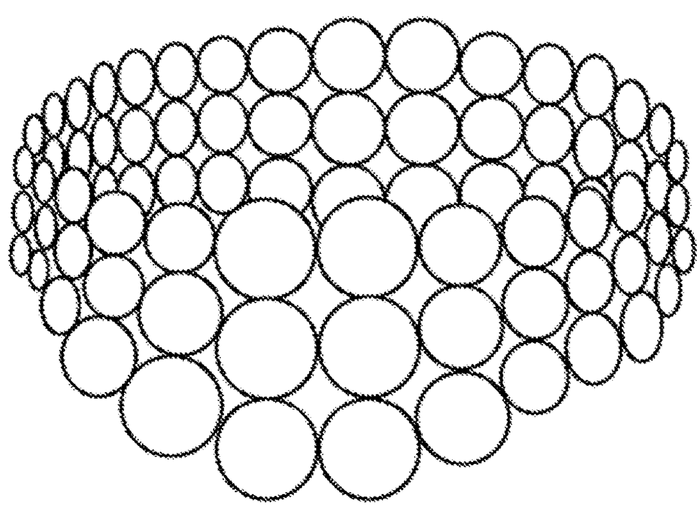
Figure 5B:
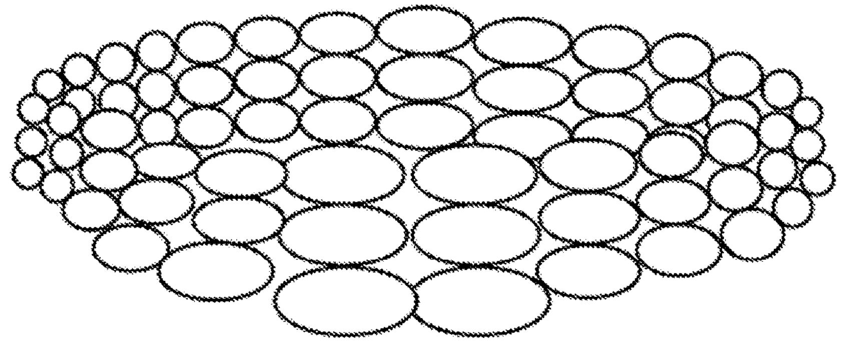

FIGS. 5A and 5B show closed sleeve-like structure comprising a plurality of closed ring-like structures. FIG. 5A shows a closed sleeve-like structure without tension and FIG. 5B shows a closed sleeve-like structure (e.g., distensible sleeve-like structure) elongated under tension.

FIGS. 6A and 6B show in accordance with embodiments herein, how the wire mesh allows for a precise fit around a body organ (e.g., a heart). FIG. 6A shows a closed ring-like structure comprising a plurality of loops secured together (see FIGS. 4A and 4B) around a heart. FIG. 6B shows a closed sleeve-like structure comprising a plurality of closed ring-like structures (see FIGS. 5A and 5B) around a heart.

FIGS. 7A, 7B, and 7C show a closed ring-like structure comprising non-overlapping fibers connecting the closed ring-like structure (e.g., the basal ring structure) to an apical hub and motor. FIG. 7A shows a cardiac sleeve comprising a closed ring-like structure (e.g., the basal ring structure) coupled to an apical hub via non-overlapping fibers (e.g., linear members) and a motor in a diastole position (e.g., relaxed). FIG. 7B shows a cardiac sleeve comprising a closed ring-like structure (e.g., the basal ring structure) coupled to an apical hub via non-overlapping fibers (e.g., linear members) and a motor in a systole position (e.g., contracted). FIG. 7C shows the motor rotation angle alpha ($\alpha$).

FIGS. 8A and 8B show a cardiac sleeve as described herein, comprising a closed ring-like structure (e.g., the basal ring structure) coupled to an apical hub via non-overlapping fibers (e.g., linear members) and a motor. In some embodiments, the cardiac sleeve described herein allows for a precise fit around a smaller body organ (e.g., a heart). For example, the non-overlapping fibers may be shortened to accommodate the smaller organ (e.g., the heart). FIG. 8A shows a closed ring-like structure (e.g., distensible ring) comprising linear members connecting the closed ring-like structure to an apical hub and motor around a smaller heart. FIG. 8B shows how the rotatable pins are positioned within the apical hub.

Figure 9:
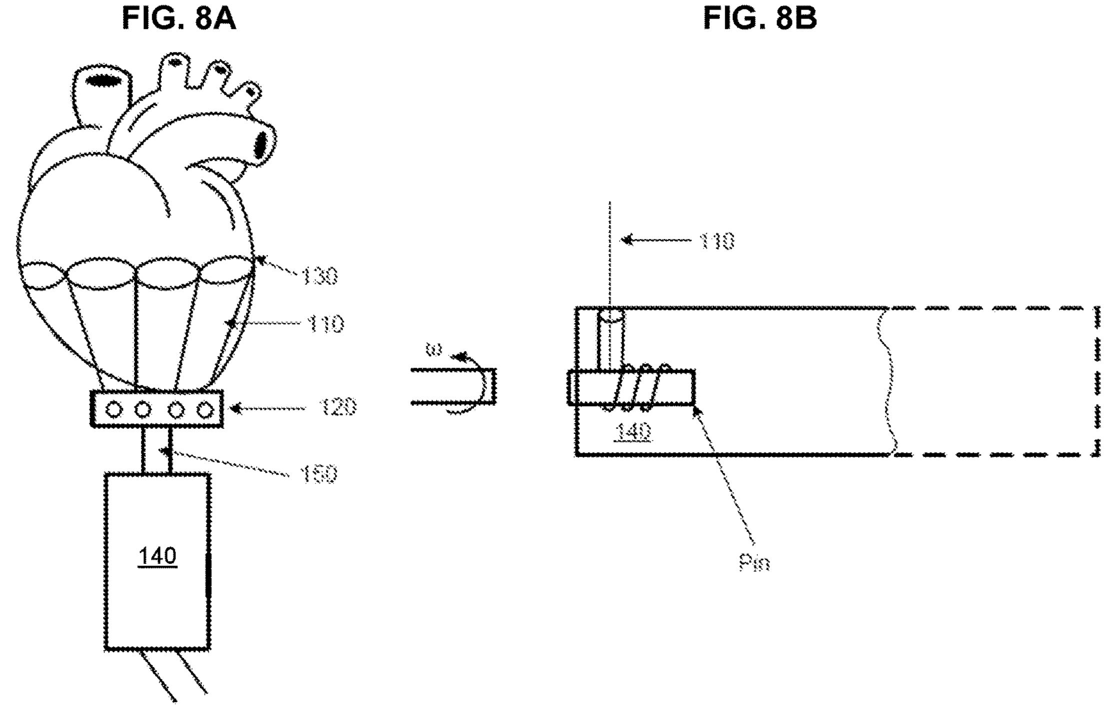

FIG. 9 shows, in accordance with embodiments herein, cardiac sleeves of the present invention.

Figure 10:
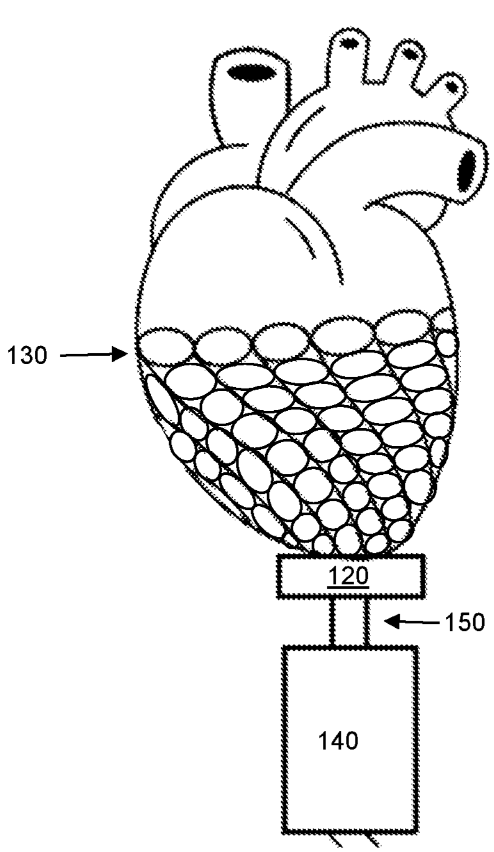

FIG. 10 shows, in accordance with embodiments herein, an adjustable cardiac sleeve comprising a basal ring structure comprising a plurality of interconnected loops coupled to an apical hub, by a plurality of adjacent ring structure. In some embodiments, the plurality of adjacent ring structures may comprise a plurality of loops that align helically between the basal ring structure and the apical hub.

DETAILED DESCRIPTION OF THE INVENTION

Following is a list of elements corresponding to a particular element referred to herein:

100 Cardiac Sleeve
110 Fiber
120 Apical Hub
130 Basal Ring Structure
131 First Loop End
132 Second Loop End
140 Actuator
150 Drive Shaft Referring now to the figures, the present invention features an adjustable cardiac sleeve (100). In some embodiments, the cardiac sleeve (100) comprises a basal ring (130) structure coupled to an apical hub (120). In some embodiments, the basal ring structure (130) comprises a plurality of interconnected loops made from a distensible wire. In some embodiments, a first loop end (131) is connected to a second loop end (132) of the interconnected loops to form a ring. In some embodiments, the basal ring structure (130) and the apical hub (120) are interconnected (e.g., coupled) to each other. The cardiac sleeves (100) described herein may be adjustable to the size of a heart.

In some embodiments, the adjustable cardiac sleeve (100) wraps around the heart and assists in the pumping function of the heart. In some embodiments, the adjustable cardiac sleeve (100) externally wraps around the still-intact heart and provides an additional pumping force via contraction and expansion of the adjustable cardiac sleeve (100). In some embodiments, the adjustable cardiac sleeve (100) externally wraps around the still-intact heart and mechanically helps contract the heart to sync with the cardiac cycle.

In some embodiments, the adjustable cardiac sleeve (100) wraps the heart externally and does not modify the native heart, and therefore, avoids direct blood contact. Because the heart remains totally intact, the patient will not die even in cases of device malfunction.

In some embodiments, the cardiac sleeve (100) is controlled by a pacemaker system (e.g., a commercially-available pacemaker; e.g., a biventricular pacemaker) to match the pace of the native, intact heart. In some aspects, a pacemaker system synchronizes the cardiac sleeve (100) and the heart to a new desired pace. In some embodiments, the cardiac sleeve (100) works only on demand in conjunction with the pacemaker system, which may conserve battery energy.

In some embodiments, the present invention describes a distensible knitted wire mesh comprising a wire curved into circular loops (see FIG. 2A) and secured where said wire crosses itself (i.e., the wire is secured at a crossing point), thus fixing the loop in place (see FIG. 1A).

In some embodiments, the basal ring structure (130) and the apical hub (120) are coupled to each other by non-overlapping fibers (110). In some embodiments, the basal ring structure (130) and the apical hub (120) are coupled to each other by helically-arranged, non-overlapping fibers (110). The non-overlapping fibers (110) may be adjustable. For example, the non-overlapping fibers (110) may be shortened or lengthened between the basal ring structure (130) and the apical hub (120) to accommodate various heart sizes (FIGS. 8A and 8B).

In some embodiments, the plurality of interconnected loops is connected via a connection component (e.g., a bead). In some embodiments, the plurality of interconnected loops is connected via a bead, e.g., a snug-fitting bead. In some embodiments, the connection component (e.g., a bead) is welded, soldered, or crimped. In some embodiments, the bead is welded, soldered, or crimped. In other embodiments, the connection component (e.g., a bead) is filled with an adhesive. In other embodiments, the bead is filled with an adhesive. As used herein, a "connection component" may refer to a cylindrical-shaped object comprising a lumen through which a wire may be passed therethrough.

In some embodiments, the plurality of interconnected loops is interlaced and secured with twists. The interlace plurality of interconnected loops may be heat set at the point at which the twist was formed. In some embodiments, interlace twists are heat set. In some embodiments, the plurality of interconnected loops is interlaced, forming crossing points. In some embodiments, the crossing points may be welded.

In certain embodiments, the wire is fixed at the crossing point (see FIG. 1A) by constraining said crossing point through a snug-fitting bead (FIG. 1B). In some embodiments, the bead (FIG. 1B) may further be filled with an adhesive (FIG. 1D), welded, soldered, or crimped (FIG. 1C). In other embodiments, the wire is fixed at the crossing point by welding (FIG. 1E).

In other embodiments, the wire is fixed by predominantly axial twist(s) around itself (FIGS. 2A and 2B). In further embodiments, the wire is fixed by predominantly orthogonal twist(s) around itself (FIGS. 2C and 2D). In some embodiments, the shape of the twist (e.g., axial or orthogonal) may be locally heat set to fix the twist in place. For example, for a super elastic or shape-memory wire (e.g., nitinol), the shape of the twist may be locally heat set to fix the twist and thus fix the loop.

In some embodiments, a plurality of loops can be constructed in sequence to create a structure of loops, where each loop will proportionately elongate in response to applied tension (e.g., a plurality of interconnected loops; see FIGS. 3A and 3B).

In some embodiments, each loop of the plurality of interconnected loops of the basal ring structure (130) is adjustable. In other embodiments, each loop of the plurality of interconnected loops of the basal ring structure (130) is expandable. In some embodiments, each loop of the plurality of interconnected loops of the basal ring structure (130) is circular (FIG. 3A). In other embodiments, each loop of the plurality of interconnected loops of the basal ring structure (130) elliptical (FIG. 3B). In other embodiments, each loop of the plurality of interconnected loops of the basal ring structure (130) expands to an elliptical shape (FIG. 3B).

In some embodiments, the structure of loops can be closed to form a distensible ring-like structure (e.g., a basal ring structure (130)) with a first loop end (131) being fixed (i.e., connected) to a second loop end (132) (FIGS. 4A and 4B).

In some embodiments, the basal ring structure (130) and the apical hub (120) are interconnected to each other by a plurality of adjacent ring structures comprising a plurality of interconnected loops, e.g., made from a distensible wire (FIG. 6B). In some embodiments, the plurality of adjacent ring structures may comprise a plurality of loops that align helically between the basal ring structure (130) and the apical hub (120)(FIG. 10). In some embodiments, the adjacent rows of ring structures are interconnected. In some embodiments, the interconnected loops are made from a distensible wire. In some embodiments, the basal ring structure (130) and the apical hub (120) are interconnected to each other by non-overlapping, helically-arranged fibers, e.g., that are enclosed within the sleeve (e.g., enclosed within a membrane).

In some embodiments, the basal ring structure (130) is coupled to the apical hub (120) by a plurality of adjacent ring structures, each ring structure comprising a plurality of interconnected loops. In some embodiments, the adjacent rows of ring structures are interconnected. In some embodiments, the basal ring structure (130) is coupled to the apical hub (120) by a plurality of adjacent ring structures (e.g., interconnected adjacent ring structures). In some embodiments, the basal ring structure (130) is coupled to the apical hub (120) via a non-overlapping fiber (e.g., helically arranged non-overlapping fibers). In some embodiments, the basal ring structure (130) is coupled to the apical hub (120) via a plurality of adjacent ring structures and non-overlapping fibers.

In some embodiments, multiple rows of ring-like structures can be interconnected to adjacent rows by techniques described herein or by interlacing the wire through the adjacent loops, allowing the construction of distensible sleeve-like structures (FIGS. 5A and 5B).

In some embodiments, the distensibility of the ring-like structure (e.g., the basal ring structure (130)) or sleeve-like structure allows the structures to distend to fit the intended purpose (FIGS. 6A and 6B). In some embodiments, the material and diameter of the loop wire and the diameter of the circular loops will affect the distention force.

In some embodiments, the structures (e.g., ring-like structure (e.g., the basal ring structure (130)) or sleeve-like structure) are made from distensible wire. In some embodiments, the distensible wire comprises a super elastic wire, e.g., that enables fiber recoil. In some embodiments, the super elastic wire is nitinol. Non-limiting examples of materials that may be used as distensible wire include but are not limited to nitinol, titanium, cobalt-chromium, stainless steel, sutures, or multifilament sutures.

In some embodiments, the cardiac sleeve (e.g., the distensible wire or fibers (110)) is coated by a soft material (e.g., polyurethane, ePTFE, etc.) to ensure bare wire/fiber does not come in contact with the heart. Non-limiting examples of a soft material that may encapsulate the sleeve (e.g., the distensible wire or fibers (110)) include but are not limited to fabric, polyurethane, expanded polytetrafluoroethylene (ePTFE), polytetrafluoroethylene (PTFE), elastomeric polymer, or silicone. In some embodiments, the soft material may comprise a hydrophilic material. In some embodiments, the soft material encapsulates the distensible wire or fibers (110).

In some embodiments, the distensible knitted mesh can be used where a structure needs to be reversibly collapsed into a smaller shape to be further expanded for a variety of uses, such as during the delivery process from a catheter or delivery device around the heart into the thoracic cavity.

In some embodiments, the cardiac sleeves (100) described herein are compressible. In some embodiments, the cardiac sleeves (100) described herein are compressed into a catheter for delivery. In other embodiments, the cardiac sleeve (100) comprising an actuator (140), as described herein, is delivered via a delivery system.

In some embodiments, the cardiac sleeve (100) is folded and/or compressed to fit into a delivery system and brought to and/or near the heart apex. Then, the cardiac sleeve (100) may be pushed out of the delivery system and maneuvered into position around the heart. In some embodiments, the delivery system is large enough to accommodate an actuator (140) which may be also loaded into the delivery system, e.g., before the sleeve. In some embodiments, the actuator (140) is preconnected to the cardiac sleeve (100) before implant.

In some embodiments, the basal ring structure (130) and the apical hub (120) are interconnected by fibers (110). In other embodiments, the basal ring structure (130) and the apical hub (120) are interconnected by non-overlapping fibers (110). In some embodiments, the basal ring structure (130) and the apical hub (120) are interconnected by helically arranged, non-overlapping fibers (110). In one embodiment, fibers (110) are incorporated into the distensible ring-like structure (i.e., the basal ring structure (130)) and attached to an apical hub (120).

In some embodiments, the non-overlapping fibers (110) are adjustable. In other embodiments, the non-overlapping fibers (110) are adjustable by rotating pins in the apical hub (120). In some embodiments, rotating the pins in the apical hub (120) changes the length of the non-overlapping fibers (110) between the basal ring structure (130) and the apical hub (120) (i.e., the length of the non-overlapping fibers (110) engaged with the heart). In some embodiments, rotating the pins in the apical hub (120) increases the length of the non-overlapping fibers (110) between the basal ring structure (130) and the apical hub (120). In other embodiments, rotating the pins in the apical hub (120) decreases the length of the non-overlapping fibers (110) between the basal ring structure (130) and the apical hub (120).

In some embodiments, the cardiac sleeve (100) described herein further comprises a membrane. In some embodiments, the membrane attaches to the basal ring structure (130) and/or the non-overlapping fibers (110). In some embodiments, the membrane is integrated with the cardiac sleeve (100). In some embodiments, the membrane may be bonded or sutured to the basal ring structure (130) and/or the non-overlapping fibers (110). In some embodiments, the cardiac sleeve (100) may encapsulate the basal ring structure (130) and/or the non-overlapping fibers (110).

In some embodiments, the membrane partially covers the cardiac sleeve (100). In other embodiments, the membrane fully covers the cardiac sleeve (100). In some embodiments, the membrane comprises natural or synthetic fiber including, but not limited to, ePTFE or Polyurethane. In some embodiments, the membrane allows the cardiac sleeve (100) to avoid direct contact with a heart. In other embodiments, the cardiac sleeve (100) described herein is partially or fully covered by a membrane to avoid direct contact with a heart.

In some embodiments, the cardiac sleeve (100) described herein further comprises an actuator (140) operably connected to the apical hub (120). In some embodiments, a drive shaft (150) connects the actuator (140) to the apical hub (120). In some embodiments, the actuator (140) is suitable for cyclic rotational or twisting motion.

The adjustable cardiac sleeves (100) described herein advantageously allow for minimally invasive surgical implantation of the sleeve.

In some embodiments, the adjustable cardiac sleeve (100) described herein only assists the heart as needed. In some embodiments, the adjustable cardiac sleeve (100) described herein continuously assists the heart.

In some embodiments, the non-overlapping fibers (110; non-overlapping, helically-arranged fibers) change their orientation from straight (FIG. 7A) to helical (FIG. 7B) according to the relative motion/twist of the cardiac sleeve (100) (i.e., according to the relative motion/twist of the actuator (140) attached to the apical ring hub (120)). As used herein, "straight," refers to a fiber that is as direct as possible between the basal ring structure (130) and the apical hub (120) while still following the contour of the surface of the heart over which the cardiac sleeve is wrapped.

In some embodiments, the cardiac sleeve (100) described herein is configured to externally wrap over the pericardium of a native, intact heart. In some embodiments, the cardiac sleeve (100) described herein is configured to externally wrap over the epicardium of a native, intact heart. In some embodiments, the cardiac sleeve (100) described herein is attached to the heart by a suture.

In some embodiments, the cardiac sleeve (100) is attached to the surface of the heart (e.g., to the epicardium or pericardium of the heart) via an anchoring mechanism, e.g., a suture. In some embodiments, the apical hub (120) and/or the basal ring structure (130) are attached to the surface of the heart (e.g., to the epicardium or pericardium of the heart) via an anchoring mechanism, e.g., a suture. In other embodiments, the cardiac sleeve (100) is attached to the surface of the heart by a hook or a suture. In other embodiments, the basal ring structure (130) of the cardiac device (100) is attached to the heart by hooks or sutures. In another embodiment, the distensible ring-like structure is attached to a heart, by means of sutures, as an example.

In some embodiments, an actuator (140) is synchronized to a heartbeat and cycles between a diastolic position (FIG. 7A) and a systolic position (FIG. 7B). In some embodiments, in the diastolic position (FIG. 7A), the fibers (110) extend around the heart from the basal ring structure (130) directly down to the apical hub (120) (e.g., the fibers are straight or linear). In some embodiments, in the systolic position (FIG. 7B), the fibers (110) are wrapped around the heart (FIG. 7B) as determined by the rotational or twist angle alpha ($\alpha$; FIG. 7C) of the actuator (140) (i.e., the fibers are helical).

In some embodiments, the non-overlapping fibers (110) are designed so that they do not elongate under the loads encountered during service; thus, the length of the fibers (110) is constant. As the fibers (110) wrap around the heart (i.e., move into a systolic position (FIG. 7B)) due to the rotational/twist angle of a, the distance between the distensible ring-like structure (i.e., the basal ring structure (130)) and the apical hub (120) will be reduced, thereby compressing the heart. Alpha (a) can be varied to control the amount of compression.

In some embodiments, the cardiac sleeve (100) described herein is adjustable to the size of the heart. In certain embodiments, the attachment position of the fibers (110) to the apical hub (120) can be adjusted to increase or shorten the distance between the distensible ring-like structure (i.e., the basal ring structure (130)) and the apical hub (120) independent of rotation/twist of the actuator (140), e.g., to fit a larger or smaller heart when the device is being implanted. This may be accomplished, for example, by coiling the fibers (110) around rotatable pins that are positioned within the apical hub (120) (FIG. 8A smaller heart, and cutaway view FIG. 8B).

The present invention may further feature a method of treating heart failure in a subject in need thereof. The method may comprise obtaining a cardiac sleeve (100) as described herein and externally wrapping over the epicardium of a native, intact heart of the subject. In some embodiments, the cardiac sleeve cycles between a diastolic position and a systolic position. In some embodiments, the diastolic position comprises fibers (110) extending linearly around the heart from the basal ring structure (130) directly down to the apical hub (120). In some embodiments, the systolic position comprises fibers (110) wrapping helically around the heart from the basal ring structure (130) directly down to the apical hub (120) and compressing the heart.

The present invention may further feature a method of treating heart failure in a subject in need thereof. The method may comprise externally wrapping a cardiac sleeve (100) as described herein over the epicardium of a native, intact heart of the subject. In some embodiments, the cardiac sleeve cycles between a diastolic position and a systolic position.

Without wishing to limit the present invention to any theory or mechanism, it is believed that the configuration of the present invention is advantageous, wherein the rings change shape (shifting towards a more elliptical shape) to allow for an expansion of overall circumference around the heart (to accommodate various heart sizes), as opposed to the material itself expanding.

As used herein, the term "about" refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of," and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. An adjustable cardiac sleeve (100) comprising:

a) a basal ring structure (130) comprising a plurality of interconnected loops interlaced with one another, wherein a first loop end (131) is connected to a second loop end (132) of the plurality of loops to form a ring;

b) an apical hub (120) coupled to the basal ring structure (130) by a plurality of non-overlapping, helically-arranged fibers; and c) an actuator (140) operably connected to the apical hub (120), wherein the actuator (140) is configured to compress a heart by actively twisting the plurality of non-overlapping, helically-arranged fibers:

wherein the adjustable cardiac sleeve (100) is attached to a surface of the heart via an anchoring mechanism.

2. The cardiac sleeve (100) of claim 1, wherein the basal ring structure (130) and the apical hub (120) are further coupled to each other by a plurality of adjacent ring structures, each ring structure comprising a plurality of interconnected loops interlaced with one another, wherein adjacent rows of ring structures are interlaced with one another.

3. The cardiac sleeve (100) of claim 1, wherein the plurality of interconnected loops is made from a distensible wire, wherein the distensible wire comprises a super elastic wire.

4. The cardiac sleeve (100) of claim 1, wherein the plurality of interconnected loops is connected via a connection component.

5. The cardiac sleeve (100) of claim 4, wherein the connection component is welded, soldered, or crimped or wherein the connection component is filled with an adhesive.

6. The cardiac sleeve (100) of claim 1, wherein the plurality of interlaced loops is secured with twists, or wherein the plurality of interlaced loops forms crossing points.

7. The cardiac sleeve (100) of claim 1, wherein the cardiac sleeve (100) is adjustable to the size of a heart.

8. The cardiac sleeve (100) of claim 1, wherein each loop of the plurality of interconnected loops of the basal ring structure (130) is adjustable and/or expandable.

9. The cardiac sleeve (100) of claim 8, wherein each loop of the plurality of interconnected loops of the basal ring structure (130) is circular.

10. The cardiac sleeve (100) of claim 8, wherein each loop of the plurality of interconnected loops of the basal ring structure (130) expands to an elliptical shape.

11. The cardiac sleeve (100) of claim 1, further comprising a membrane.

12. The cardiac sleeve (100) of claim 11, wherein the membrane partially or fully covers the cardiac sleeve (100).

13. The cardiac sleeve (100) of claim 12, wherein the membrane comprises natural or synthetic fiber.

14. The cardiac sleeve (100) of claim 11, wherein the membrane allows the cardiac sleeve (100) to avoid direct contact with a heart.

15. The cardiac sleeve (100) of claim 1, further comprising a drive shaft (150) connecting the actuator (140) to the apical hub (120).

16. The cardiac sleeve (100) of claim 1, wherein the cardiac sleeve (100) is configured to externally wrap over the epicardium of a native, intact heart.

17. The cardiac sleeve (100) of claim 1, wherein the basal ring structure is attached to the heart by an anchoring mechanism.

18. A method of treating heart failure in a subject in need thereof, the method comprising:

a) obtaining a cardiac sleeve (100) comprising:

i) a basal ring structure (130) comprising a plurality of interconnected loops interlaced with one another, wherein a first loop end (131) is connected to a second loop end (132) of the plurality of interconnected loops to form a ring:

ii) an apical hub (120) coupled to the basal ring structure (130) by a plurality of non-overlapping, helically-arranged fibers; and iii) an actuator (140) operably connected to the apical hub (120);

b) externally wrapping the cardiac sleeve (100) over an epicardium of a native, intact heart of the subject, and c) attaching the cardiac sleeve to the epicardium of the native, intact heart via an anchoring mechanism, d) operating the actuator (140) to cycle the cardiac sleeve (100) between a diastolic position and a systolic position.

19. The method of claim 18, wherein the plurality of non-overlapping, helically-arranged fibers are configured to compress the heart when the cardiac sleeve is in the systolic position.

* * * * *